United States Patent [19]

Berchadsky et al.

[11] Patent Number: 5,006,663

[45] Date of Patent: Apr. 9, 1991

[54] PHOSPHORUS-CONTAINING CYCLIC NITROXIDE FREE RADICALS

[75] Inventors: Yves Berchadsky, Marseille; Nelly Kernevez, Grenoble; Francois Le Moigne; Anne Mercier, both of Marseille; Liliane Secourgeon, Saint Egreve; Paul Tordo, Marseille, all of France

[73] Assignee: Commissariat a l'Energie Atomique, Paris, France

[21] Appl. No.: 433,597

[22] Filed: Nov. 8, 1989

[30] Foreign Application Priority Data

Nov. 21, 1988 [FR] France ................... 88 15107

[51] Int. Cl.$^5$ .......................... C07F 9/40; C07F 9/42; C07F 9/44; C07F 9/53
[52] U.S. Cl. .................................................. 548/412
[58] Field of Search ........................................ 548/412

[56] References Cited

U.S. PATENT DOCUMENTS 3,966,409  6/1976  Hrvoic et al. .................... 436/173

FOREIGN PATENT DOCUMENTS 0185825  7/1986  European Pat. Off. .

Primary Examiner—Robert W. Ramsuer
Assistant Examiner—Michael G. Ambrose
Attorney, Agent, or Firm—Michael N. Meller

[57] ABSTRACT

A nitroxide radical of the formula (I) or (II):

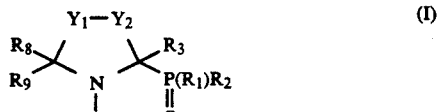

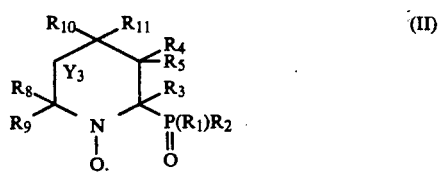

in which $R_1$ and $R_2$ are independently chosen from among the optionally deuterated alkyl, alkoxyl, dialkylaminyl and phenyl radicals, H, D or Cl; $R_3$, $R_8$ and $R_9$ are independently chosen from among the optionally deuterated alkyl, alkoxyl and phenyl radicals; $R_4$, $R_5$, $R_6$ and $R_7$ are independently chosen from among the optionally deuterated alkyl, alkoxyl, dialkylaminyl and phenyl radicals, COOH, OH, OD, H, D, a halogen, COOR (in which R is an alkyl radical); $R_{10}$ and $R_{11}$ are independently chosen from among optionally deuterated alkyl, alkoxyl, dialkylaminyl and phenyl radicals, COOH, OH, OD, H, D, a halogen, COOR (in which R is an alkyl radical) or represent an oxygen atom linked with the cycle of the radical by a double bond is described.

4 Claims, No Drawings

PHOSPHORUS-CONTAINING CYCLIC NITROXIDE FREE RADICALS

DESCRIPTION

The invention relates to novel free, cyclic nitroxide radicals and to their production process. These radicals, which are stable in solution, are used in magnetometry in a weak magnetic field using nuclear magnetic resonance (NMR) with dynamic polarization of the nuclei of the solvent in which are dissolved said radicals (OVERHAUSER/ABRAGAM effect).

Apart from magnetometry, stable, cyclic nitroxide radicals can be used in numerous other fields and in particular as spin markers, contrast agents for NMR imaging, relaxing agents, nuclear dynamic polarizing agents, stabilizing or modifying agents in polymer chemistry, or as photosensitizing agents or anti-tumour agents in pharmacology.

In order to be stable in solution, a nitroxide radical must not have a hydrogen atom in the alpha position of the group (N—O), the presence of hydrogens causing a dismutation reaction leading to a nitrone and a hydroxylamine. Thus, the cyclic nitroxides frequently used in the aforementioned applications have structures of type:

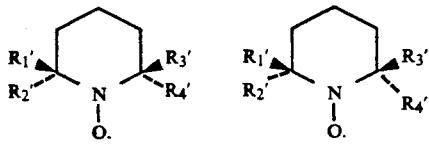

in which $R_{1'}$, $R_{2'}$, $R_{3'}$ and $R_{4'}$ are all alkyl groups, whereby different substituent types can be present on the other carbons of the piperidine and pyrollidine cycles.

These nitroxide radicals have hyperfine couplings between the electron and nitrogen nucleus, whose value, measured by electron paramagnetic resonance, is approximately 1.6 mT and reaches approximately 2 mT when the nitrogen 14 is replaced by its $^{15}N$ isotope.

The presently known nitroxide radicals and their use in magnetometry are in particular described in U.S. Pat. No. 3,966,409, EP-A-0 185 825, the article in the Journal de Physique, vol.36, June 1975, pp.571-580 by Y. AYANT et al and entitled "Experimental and Theoretical Study of the Width of EPR Lines of TANONE in Solution".

In the magnetometry field, the principle used is the nuclear magnetic resonance of protons with a dynamic polarization. The sensitivity of magnetometers expresses the possibility of detecting a certain abnormality of the magnetic field at a given distance. The sensitivity of a magnetometer increases with the value of the dynamic polarization factor (DPF) of radical solutions.

The study of the TANO radical corresponding to 2,2,6,6-tetramethyl-4-piperidon-1-oxyl has made it possible to establish an expression of this polarization factor of type:

$$(DPF) = (2fx\sqrt{e}/nx\sqrt{H})F$$

in which f is the electron-proton coupling leak factor translating the relaxation of the proton of the solvent containing the radical by interactions other than that of the coupling with the electron of the radical, n is the number of energy levels of the radical, $\sqrt{e}$ the centre frequency of the electron resonance, which increases with the hyperfine coupling constant of the radicals, $\sqrt{H}$ is the resonant frequency of the solvent proton and F is a function of the electron relaxation time of the radical.

This expression reveals the increase of the DPF and consequently that of the sensitivity of the magnetometer with the hyperfine coupling of the radical.

The presently most advantageous nitroxide radical in magnetometry is TANO d15N corresponding to 2,2,6,6-tetramethyl-4-piperidon-1-oxyl of the perdeuterated 15 nitrogen form.

The present invention relates to novel free nitroxide radicals and their production process, usable in magnetometry and in particular making it possible to increase the sensitivity of these magnetometers with a view to the detection of a weaker magnetic field abnormality, in which the latter has a greater distance than in the case of the prior art magnetometers.

The present invention therefore relates to a cyclic nitroxide radical having formula (I) or formula (II):

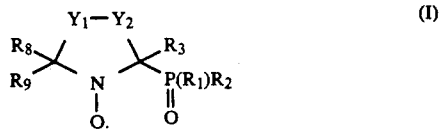 (I)

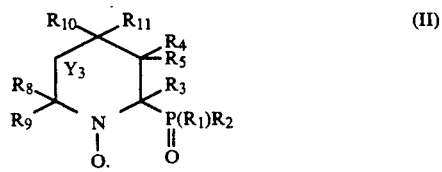 (II)

in which $Y_1$ represents

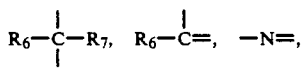

or an oxygen atom, $Y_2$ represents

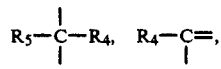

$Y_3$ represents

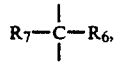

or an oxygen atom and when $Y_1$ represents

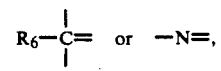

then $Y_2$ exclusively represents

and when $Y_1$ represents

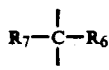

or an oxygen atom, $Y_2$ exclusively represents

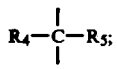

$R_1$ and $R_2$ being independently chosen from among the optionally deuterated alkyl, alkoxyl, dialkylamino and phenyl groups, hydrogen atoms, deuterium or chlorine; $R_3$, $R_8$ and $R_9$ are independently chosen from among the optionally deuterated alkyl, alkoxyl and phenyl groups; $R_4$, $R_5$, $R_6$ and $R_7$ are independently chosen from among the optionally deuterated alkyl, alkoxyl, dialkylamino and phenyl groups, COOH, OH, OD, H, D, a halogen, COOR (in which R is an alkyl group); $R_{10}$ and $R_{11}$ are independently chosen from among the optionally deuterated alkyl, alkoxy, dialkylamino and phenyl groups, COOH, OH, OD, H, D, a halogen, COOR (in which R is an alkyl radical), or represents an oxygen atom linked to the cycle of the radical by a double bond.

The beta-phosphorus nitroxide radicals according to the invention are good candidates for dynamic polarization NMR magnetometry, because they have higher hyperfine electron-nucleus couplings of the phosphorus than the known nitroxides presently used in magnetometry. Preferably, in formulas (I) or (II) of the nitroxide radicals according to the invention, $Y_2$ represents

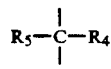

and $Y_1$ and $Y_3$ represent

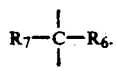

The alkyl, alkoxyl and dialkylamino groups usable in the invention can be straight-chained or branched, or cyclic and have to 18 carbon atoms. Moreover, all or part of their hydrogen atoms can be replaced by deuterium atoms. Preference is given to the use of alkyl, alkoxyl and dialkylamino groups with 1 to 6 carbon atoms.

Usable alkoxyl groups are methoxyl, ethoxyl, isopropoxyl and phenoxyl groups, which may be deuterated. Alkyl groups usable in the invention are methyl, ethyl, isopropyl or t-butyl groups. These groups can also be deuterated, such as e.g. $CD_3$, $CD_2CD_3$. Dialkylamino groups usable in the invention are dimethylamino, dielhylamino, diisopropylamino, and dibutylamino.

In the preferred nitroxide radicals according to the invention, $R_{10}$ represents H, D, OH, or an alkyl group, such as the methyl, ethyl, isopropyl or t-butyl group, or a phenyl radical; $R_4$, $R_5$, $R_6$, $R_7$ and $R_{11}$ can represent in particular H or D. Moreover, $R_{10}$ and $R_{11}$ can represent an oxygen atom linked to the piperidine cycle by a double bond. Finally, $R_1$ and $R_2$ represent an aforementioned alkoxyl group and $R_3$, $R_8$ and $R_9$ a phenyl group or an alkyl group, which can optionally be deuterated in the manner indicated hereinbefore.

The nitroxide radicals according to the invention can advantageously be used in magnetometry. To this end, the invention also relates to a process for dynamic polarization in a weak field of nuclei of a solvent by saturation of an electron magnetic resonance line of a free radical with a hyperfine spectral structure, as described hereinbefore, dissolved in said solvent.

For use in magnetometry, preference is given to:

2-diethoxyphosphoryl-2,5,5-trimethyl-pyrrolidin-1-oxyl, hereinafter called TOMER and satisfying the formula

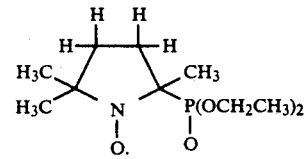

2-diethoxyphosphoryl-4-phenyl-2,5,5-trimethyl-pyrrolidin-1-oxyl, hereinafter called TOBER and having the formula

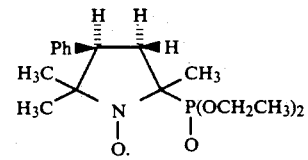

or its deuterated homolog called TOBER d11 of formula

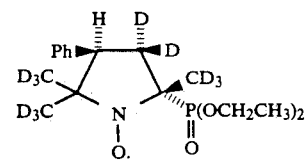

with Ph representing a phenyl group.

The invention also relates to a process for the preparation of nitroxide radicals satisfying the above general formulas (I) or (II). These radicals can be obtained by the addition of dialkyl phosphonate of formula (V)

to a nitrone of formula (X)

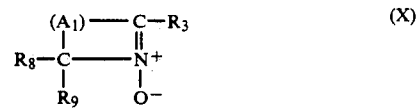

with $A_1$ representing $$-\underset{\underset{R_7}{|}}{\overset{\overset{R_6}{|}}{C}}-\underset{\underset{R_5}{|}}{\overset{\overset{R_4}{|}}{C}}-$$

and Z representing H or D, said addition being followed by an oxidation using in particular, copper acetate.

Use is made of Z=D, when it is wished to obtain a nitroxide radical in which all or part of $R_3$, $R_4$, $R_5$, $R_6$, $R_7$, $R_8$ and $R_9$ represents a deuterium atom or a deuterated alkyl, alkoxyl, phenyl or dialkylamino group.

This process has an improved reactivity when $R_3$ represents the methyl group. This process makes it possible to obtain TOBER and TOMER nitroxide radicals. The operating procedure is in particular that described in the article by J.M.J. TRONCHET et al, Helv. Chem. Acta., vol.68, p.1893, 1985.

The nitrones of formula (X) can be prepared by cyclization of nitroketones of formula (XI)

$$R_8-\underset{\underset{NO_2}{|}}{\overset{\overset{R_9}{|}}{C}}-(A_1)-\underset{\underset{R_3}{|}}{C}=O \qquad (XI)$$

This cyclization involves a first stage of reducing the nitroketone by zinc in the presence of $NH_4Cl$ in aqueous solution, followed by an acidification stage, in particular by HCl. The operating procedure for producing nitrones and nitroketones is in particular that described in the article by J. B. BAPPAT et al, Aust. Phys. Chem., vol.21, pp.2483-2495, 1968.

For obtaining the nitroxide radicals according to the invention, it is possible to replace the dialkyl phosphonate (V) by its lithium salt. The operating procedure is that described in the article by A. VASELLA, Helv. Chem. Acta, vol.68, p.1730, 1985.

This process for obtaining nitroxide radicals is relatively complex in the case of cumbersome $R_3$ groups. Moreover, the yields are low and the purification of the nitroxides relatively difficult. Thus, this process is not completely suitable for the mass production on an industrial scale of nitroxide radicals according to the invention.

In addition, it is preferred to produce the nitroxide radicals according to the invention by another process based on the cyclization of aminoalkenyl phosphonates. This process gives a 60% yield compared with the starting amino alkenylphosphonate.

According to the invention this process comprises:
forming a cyclic amine of formula (III)

$$\begin{array}{c} R_3 \\ | \\ (A_2)-C-P(R_1)R_2 \\ | \quad | \quad \parallel \\ R_8-C-N \quad O \\ | \quad \backslash R_{14} \\ R_{12}-C-H \\ | \\ R_{13} \end{array} \qquad (III)$$

by cyclizing aminomercuration, followed by a demercuration by sodium hydridoborate or deuteroborate, of an amino alkenylphosphonate of formula (IV)

$$\begin{array}{c} R_3 \quad O \\ | \quad \parallel \\ R_8 \quad (A_2)-C-P(R_1)R_2 \\ \backslash C \quad | \\ \parallel \quad N-Z \\ C \quad | \\ / \quad \backslash \quad R_{14} \\ R_{12} \quad R_{13} \end{array} \qquad (IV)$$

in which $R_{12}$, $R_{13}$ and $R_{14}$ independently represent optionally deuterated alkyl groups, a hydrogen atom or a deuterium atom, Z representing H or D and $(A_2)$ representing $$-\underset{\underset{R_7}{|}}{\overset{\overset{R_6}{|}}{C}}-\underset{\underset{R_5}{|}}{\overset{\overset{R_4}{|}}{C}}- \quad \text{or} \quad -\underset{\underset{R_7}{|}}{\overset{\overset{R_6}{|}}{C}}-\underset{\underset{R_{10}}{|}}{\overset{\overset{R_{11}}{|}}{C}}-\underset{\underset{R_5}{|}}{\overset{\overset{R_4}{|}}{C}}-$$

and oxidizing the cyclic amine by m-chloroperbenzoic acid.

It would also be possible to envisage another oxidant, such as $H_2O_2$ in the presence of phosphotungstic acid as the catalyst.

Advantageously, the amino alkenylphosphonate is formed by reacting a dialkyl phosphonate of formula (V)

$$\underset{O}{\overset{\parallel}{ZP(R_1)R_2,}}$$

Z representing H or D, on an enone of formula (VI)

$$\begin{array}{c} R_8 \quad (A_2) \quad R_3 \\ \backslash / \quad \backslash / \\ C \quad C \\ \parallel \quad \parallel \\ C \quad O \\ / \backslash \\ R_{12} \quad R_{13} \end{array} \qquad (VI)$$

in the presence of $NH_3$, $ND_3$ or an amine $NH_2R_{14}$ and an ammonium halide of hexamethyl phosphorus triamide (HMPT), heated to less than 100° C. and in particular to 50° C.

This aminophosphorylation using gentler experimental conditions than those generally used makes it possible to obtain very pure products with a yield of at least 60% compared with enone, said result being comparable to those obtained by the methods recommended in the article by YU. P. BELOV, Bull. Akad. Sci.SSSR, div. Chem. Sci., p.1467, 1976 and FIELD J., Am. Chem. Soc., vol.74, p.1528, 1952.

In the process for the production of nitroxide radicals according to the invention with $R_4$ or $R_5$ representing H, the enone is formed by reaction in an organic medium of an alkenyl chloride of formula (VII)

$$\begin{array}{c} R_{12} \quad B-Cl \\ \backslash \quad / \\ C=C \\ / \quad \backslash \\ R_{13} \quad R_8 \end{array} \qquad (VII)$$

in which B represents

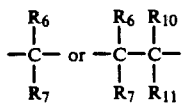

with an ester of formula (VIII)

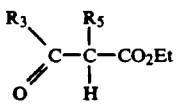

in which ET represents the ethyl group, in the presence of sodium alkoxide, followed by saponification and decarboxylation.

In the process according to the invention, when $Y_2$ represents

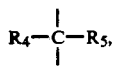

it is possible to produce the enone by reacting an alkenyl bromide or chloride of formula (XII)

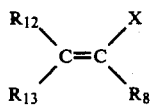

in which X represents Cl or Br with a compound of formula (XIII)

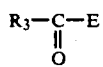

in which E represents

in the presence of magnesium or cuprous iodide, in an organic medium.

The invention also relates to a process for the preparation of an amino alkenylphosphonate for the production of nitroxide radicals and consisting of reacting a dialkyl phosphonate of formula (V)

with Z equals H or D with an enone of formula (VI)

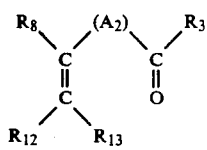

with $(A_2)$ representing

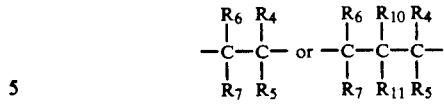

in the presence of $NH_3$, $ND_3$ or an amine $NH_2R_{14}$ and an ammonium halide in HMPT heated to a temperature below 100° C., whereby in these formulas $R_1$ and $R_2$ are independently chosen from among optionally deuterated alkyl, alkoxyl, dialkylamino and phenyl groups and hydrogen, deuterium or chlorine atoms; $R_3$, $R_8$ and $R_9$ are independently chosen from among optionally deuterated alkyl, alkoxyl and phenyl groups; $R_4$, $R_5$, $R_6$ and $R_7$ are chosen independently from among optionally deuterated alkyl, alkoxyl, dialkylamino and phenyl groups, COOH, OH, OD, H, D, a halide, COOR (in which R is an alkyl radical); $R_{10}$ and $R_{11}$ are chosen independently from among optionally deuterated alkyl, alkoxyl, dialkylamino and phenyl groups, COOH, OH, OD, H, D, a halogen, COOR (in which R is an alkyl group), or represent an oxygen atom bonded to the cycle of the radical by a double bond.

Other features and advantages of the invention can be gathered from the following illustrative and non-limitative description. In particular, other processes for producing nitroxide radicals according to the invention will be illustrated therein.

The beta-phosphorus nitroxide radicals according to the invention complying with formulas (I) or (II) have been characterized in electron paramagnetic resonance (EPR) with a high magnetic field (approx 0.33 T). These radicals are stable in solution and have hyperfine coupling constants of up to 9 mT.

Nuclear dynamic polarization measurements were carried out on solutions containing radicals according to the invention in the earth's magnetic field using a NMR spectrometer produced according to the BLOCH configuration described in the article by M. SAUZADE, NMR and EPR Spectrometers, Technique de l'ingenieur E4350 1-7, E4351 1-24.

The following table gives the characteristics of several betaphosphorus nitroxide solutions at a concentration of mM in tetrahydrofuran (THF). These characteristics are compared with those of the radical TANO 14N and TANO d15N. The latter is at present the best of the nitroxide radicals for magnetometry (cf EP-A-0 185 825 or FR-A-2 546 518).

In this table, $\sqrt{e}$ is the electron resonance frequency of the radical, n the energy level number, values appearing in the expression of the dynamic polarization factor given hereinbefore and $S_N$ the amplitude of the nuclear dynamic polarization signal of the radical solution.

It can be clearly gathered from this table that the nitroxide radicals according to the invention can replace the presently known nitroxides for magnetometry applications. In particular the deuterated TOBER d11 radical can advantageously replace the TANO d15N radical.

The nitroxide radicals according to the invention can in particular be used in the magnetometer described in EP-A-0 185 825.

A description will now be given of the synthesis of certain beta-phosphorus cyclic nitroxides according to the invention. For simplification purposes, this synthesis is described hereinafter for the TOMER and TOBER radicals, as well as for the 2-diethoxyphosphoryl-2,6,6- trimethyl-piperidine-1 oxyl radical, called TANAPE and having the formula (II) in which:

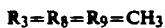

These radicals are prepared by cyclizing aminomercuration, followed by demercuration by sodium hydridoborate of an amino alkenylphosphonate of formula (IVa), (IVb) or (IVd), given in appendixes I and III for forming cyclic amines respectively of formulas (IIIa), (IIIb) and (IIId) as indicated in the appendixes, using the Perie method, Tetrahedron, vol.28, pp.675–699, 1972.

These cyclic amines are then oxidized by m-chloroperbenzoic acid to respectively give the TOMER, TANAPE and TOBER radicals.

Experimentally, the amino alkenylphosphonates (IVa), (IVb) and (IVd) are treated by stoichiometric quantities of mercuric acetate ($CH_3CO_2)_2Hg$ in suspension in strictly purified tetrahydrofuran. The reaction mixture is then treated by a slight sodium hydridoborate deficiency ($NaBH_4$), dissolved in a 2.5M aqueous soda solution.

After saturation of the aqueous solution by sodium chloride, the organic phase is extracted with ether and then dried on magnesium sulphate. After evaporation of the solvent, a crude mixture is obtained, which contains the amine (IIIa), (IIIb) or (IIId) accompanied by 10 to 20% of the starting product.

In the case of amine (IIIa), the crude mixture obtained after cyclization, taken up by pentane, allows the deposition of white crystals, whose melting point is 51° to 52° C. In the case of amine (IIId), 2 diastereoisomers are obtained in the form of oil, which is separated by liquid chromatography.

Percentage analysis and analysis of the NMR $^1H$ and $^{13}C$ spectra are completely in accordance with structures (IIIa) and (IIId).

In the case of amine (IIIb), the crude mixture obtained after cyclization in the form of a yellow oil is treated by a picric acid equivalent dissolved in a minimum of methanol. The solution permits the deposition of red crystals of the picrate corresponding to (IIIb), the melting point being 109° C. The percentage analysis and the analysis of the $^1H$ NMR spectrum of the picrate are in perfect accordance with structure (IIIb).

To a solution ($4 \cdot 10^{-3}$ mole) of cyclic amines (IIIa), (IIIb) or (IIId) in 10 ml of ethyl ether are added dropwise at 0° C. $5 \cdot 10^{-3}$ mole of m-chloroperbenzoic acid dissolved in 5 ml of ether. At the end of addition, the reaction is allowed to continue for 8 hours at ambient temperature.

The solution is then neutralized by a potassium carbonate excess, followed by extraction with ether. The thus obtained organic phase is successively washed by a sodium chloride-saturated water solution and then by a dilute sulphuric acid solution. The ethereal radical solution is dried on sodium sulphate. Evaporation of the ether leads to a coloured oil.

The radicals obtained are then purified by thin layer chromatography of 1 mm. The support is a Merck 60 F254 silica gel and the eluent used is a mixture of tetrahydrofuran, ether, pentane and chloroform in the proportions 1/1/4/2. The radicals are collected with yields of approximately 30 to 40%.

The amino alkenylphosphonates (IVa), (IVb) and (IVd), precursors of the TOMER, TANAPE and TOBER radical synthesis, are prepared by enone aminophosphorylation. To this end, a diethyl phosphonate of formula

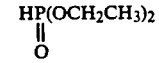

is reacted on an enone of formula (VIa), (VIb) or (VId) as indicated in appendixes I and III. This aminophosphorylation takes place in the presence of ammonium chloride dissolved in hexamethyl phosphotriamide heated to 50° C. into which ammonia is bubbled.

The enones of formulas (VIa) and (VIb) are obtained in two stages according to the procedure of S. SCHECHTER et al, described in J. Am. Chem. Soc., 71(7), 1949, pp.3165–3173.

These enones are formed by reacting an alkenyl chloride of formula (VIIa) or (VIIb), as given in appendix II, on an ester of formula (VIIIa), in the presence of sodium ethanolate, in ethanol leading to the compounds (IXa), or (IXb) given in appendix II. These compounds (IXa) and (IXb) then undergo saponification with potash, followed by decarboxylation using sulphuric acid. This decarboxylation is performed under reflux.

The enone of formula (VId) is advantageously obtained by reacting an alkenyl chloride (VIId) on an ethylene ketone (VIIId) according to the Michael addition 1–4. This process is based on the method described in Organic Reaction, vol.19, pp.1–113, chapter I, by G. H. POSNER.

Experimental conditions for the preparation of radicals according to the invention will now be given.

EXAMPLE I

Obtaining the TOMER Radical (a) Preparation of 5-methyl-5-hexen-2-one of formula (VIa)

To a sodium ethylate solution prepared with 23 g (1 mole) of sodium in 300 ml of anhydrous ethanol are added at 15° C. 143 g (1.1 mole) of ethyl acetyl acetate (formula (VIIIa)). 30 minutes after the end of the addition 90.5 g (1 mole) of methallyl chloride (formula (VIIa)) are added. After reacting for 12 hours, the reaction mixture is filtered, reconcentrated on the rotary evaporator and distilled under a reduced pressure. The 95° to 97° fraction is collected at 20 mb ($2 \cdot 10^3$ Pa), namely 104 g of ethyl-2-acetyl-4-methyl-4-pentenoate (formula (IXa)), namely a yield of 51.5% based on the ethyl acetyl acetate (the product is checked by gas chromatography on a SE 30 column with 10% on a chromosorb 1.4 m, 120° to 150° C.).

The following stages relate to saponification and decarboxylation.

To an aqueous potash solution (25 g of potash in 170 ml of water) at 0° C. are added in 90 minutes, 73 g of ethyl-2-acetyl-4-methyl-4-pentenoate (formula (IXa)). After dissolving, it is left for 4 days at 4° C. in the refrigerator. After separating the supernatant residual oil, 15 ml of sulphuric acid are added in 25 ml of water and heating takes place for 18 hours at 70° C. $CO_2$ release makes it possible to follow the evolution of the reaction.

The supernatant organic phase is separated, the sodium chloride-saturated aqueous phase extracted with petroleum ether and then with ethyl ether. The recombined organic phases are washed with an aqueous sodium bicarbonate solution and then with a sodium chloride solution, followed by drying on sodium sulphate. Distillation takes place under 80 mbar (8·10³ Pa). The 50° to 70° fraction is 5-methyl-5-hexen-2-one (compound (VIa), which represents 31 g corresponding to a 70% yield.

The magnetic resonance characteristics of the product obtained are as follows:

NMR ¹H (60 MHz) (CDCl₃) δ (ppm)

ethyl 2-acetyl-4-methyl-4-pentenoate: 1.22 (t, 3H, ester methyl), 1.72 (s, 3H, methyl in $C_5$), 2.25 (s, 3H, protons in $C_1$), 2.55 (d, 2H, protons in $C_4$), 3.60 (t, 1H, proton in $C_3$), 4.17 (q, 2H, methylene of ester), 4.65 and 4.72 (s, 1H, protons in $C_6$).

5-methyl-5-hexen-2-one: 1.7 (s, 3H, methyl in $C_5$), 2.15 (s, 3H, protons in $C_1$), 2.45 (massive, 4H, protons in $C_3$ and $C_4$), 4.6, (s, 2H, protons in $C_6$); with t=triplet; s=singlet; d=doublet; δ position of the singlet, doublet, ...; q=quintuplet; CDCl₃=solvent.

(b) Preparation of diethyl (1-amino-1,4-dimethyl-4-pentene)-phosphonate (formula (IVa))

To 0.05 g (0.02 mole) of ammonium chloride (NH₄Cl) in 4 ml of HMPT are added at 60° C. and under ammonia bubbling 5 g (0.045 mole) of 5-methyl-5-hexen-2-one (compound VIa) and then 6.9 g (0.05 mole) of diethyl phosphonate. After 2 hours, the reaction mixture is acidified by a solution of 4.42 g of 12N hydrochloric acid diluted in water. The HMPT is extracted and the residual phosphonate is extracted with ether. The amine is separated by adding potassium carbonate and potassium chloride. The product is extracted with ether and drying takes place on anhydrous sodium sulphate.

After distilling in the ball oven (30° C., 7 mb 7·10² Pa), 6.8 g of diethyl (1-amino-1,4-dimethyl-4-pentene)-phosphonate are collected, namely compound (IVa) with a yield of 60% based on the enone (VIa). The magnetic resonance characteristics of the product obtained are as follows:

NMR ¹H (60 MHz) (CDCl₃): δ (ppm): 1.25 (d, J(H-P)=16 Hz, 3H, methyl in $C_1$), 1.30 (t, J(H-H)=7 Hz, 6H, methyls of phosphonate), 1.71 (s, 3H, methyl in $C_4$), 2.0 (massive, 6H, methyls in $C_2$ and $C_3$, protons of the amine), 4.15 (multiplet, J(H-H)=7 Hz, 4H methylene of phosphonate, 4.70 (s, 2H, protons in $C_5$).

J(H-P)=16 Hz is the coupling between the proton and P of the radical; J(H-H)=coupling of a proton with another proton of the radical.

NMR ³¹P (CDCl₃): δ (ppm): 30.6

Microanalysis: % expected: C 53.01; H 9.64; N 5.62; % found: C 52.23; H 9.69; N 5.73.

(c) Preparation of diethyl(2,5,5-trimethyl-2-pyrrolidinyl)phosphonate of formula (IIIa)

To a suspension of 6.37 g (0.02 mole) of mercuric acetate in 300 ml of acetone are added 5.15 g of diethyl(1-amino-1,4-dimethyl-4-pentene)phosphonate (formula (IVa)). After reacting for 4 hours at ambient temperature, the acetone is evaporated. This mercuric compound, taken up by THF, is reduced by 0.57 g of sodium hydridoborate in 7 ml of a soda solution (2.5 mole). The reaction mixture is saturated by adding potassium carbonate and potassium chloride, extracted with ether and dried on sodium sulphate.

On the basis of the ¹H NMR of the crude product, there is a 60% conversion rate, the product, taken up in 10 ml of pentane, crystallizing at −20° C. 4.7 g of cyclic aminophosphonate (IIIa) are collected, melting point 51° to 52° C.

The magnetic resonance characteristics of the product obtained are as follows:

NMR ¹H(200 MHz) (CDCl₃): δ (ppm):

1.18 and 1.24 (s, 3H, methyls in $C_5$), 1.33 and 1.34 (t, J(H-H)=7 Hz, 3H, methyls of phosphonate), 1.40 (d, J(H-P)=16 Hz, methyl in $C_2$), 1.77 (m, 3H, 2 protons in $C_4$, 1 proton in $C_3$), 2.37 (m, 1H, 1 proton in $C_3$)), 4.18 (m, 4H, protons of the methylenes of phosphonate), 1.18 to 1.44 (s, 1H, proton of the amine).

NMR ³¹P(CDCl₃): δ (ppm)29.21.

Microanalysis: % calculated: C 53.01; H 9.64; N 5.62. % found: C 53.23; H 9.31; N 6.02.

(d) Obtaining 2-diethylphosphonyl-2,5,5-trimethyl-pyrrolidin-1-oxyl (TOMER)

To 3.5 g of diethyl(2,5,5-trimethyl-2-pyrrolidinyl)-phosphonate (IIIa) in 70 ml of ether at 0° C. is added a solution of 4.30 g of metachloroperbenzoic acid (85.6% in 30 ml of ether). After 2½ hours of reaction, neutralization takes place with a saturated aqueous sodium bicarbonate solution. Successive washing operations are carried out with water, 1N sulphuric acid, water, sodium bicarbonate and water. After drying on sodium sulphate and reconcentration, 2.10 g of oily green residue are obtained. The product undergoes chromatography three times on a silica 60 preparation plate (eluants:- 1:ethyl ether; 2 and 3:THF/chloroform 1/1 by volume). 0.92 g of TOMER beta-phosphorus nitroxide are obtained.

The TOMER radical is a pale yellow oil with the following characteristics:

EPR (deoxygenated benzene): six lines A(¹⁴N)-13.5 G, A(³¹P)=50.0 G, ΔH$_{pp}$=1.4 G UV=240 mm (in acetonitrile).

Mass spectrum m/e (70 ev), 264 (M+), 249 (M+-CH₃), 127 (M+-P(O)(OEt)₂).

EXAMPLE 2

Obtaining the TOBER radical (a) Preparation of 5-methyl-4-phenyl-5-hexen-2-one of formula (VId)

The reaction is performed in an inert atmosphere with freshly distilled solvents. To 29 g of magnesium turnings in THF are slowly added 12.5 g (0.10 mole) of 2-bromopropene dissolved in 100 ml of THF. The addition rate is regulated so as to maintain a slight reflux. At the end of addition, reflux is maintained for 90 minutes.

The organo magnesium compound is then added to a solution of 10 g (0.068 mole) of benzalacetone and 7% (0.97 g) of CuI in 250 ml of THF. The mixture rapidly assumes a brown colouring. After addition, it is left for a few minutes at reflux and then 12 hours at ambient temperature. Hydrolyzing takes place by the addition of the reaction mixture to crushed ice and ammonium chloride, accompanied by very vigorous stirring. After 2 hours, the mixture assumes a blue lavender shade. Extraction takes place with ether and the product is dried on sodium sulphate.

By distillation in the ball oven, the 120° C. fraction is collected at 1 mb (10² Pa): 5-methyl-4-phenyl-5-hexen-2-one, 4.4 g, i.e. a yield of 35% based on the benzalacetone.

The characteristics of the product obtained are as follows:

NMR $^1$H (60 MHz)(CDCl$_3$): δ (ppm):

1.55 (s, 3H, methyl in C$_5$), 2.0 (s, 3H, protons in C$_1$), 2.85 (m, 2H, protons in C$_3$), 3.75 (, 1H, proton in C$_4$), 4.80 (s, 2H, protons in C$_6$), 7.2 (massive, 5H, protons of phenyl).

Mass spectrum (CPV coupling/mass spectrometry): molecular peak at M/e=188.

(b) Preparation of diethyl-1-amino-4-phenyl-1,4-dimethyl-1-pentene)-phosphonate of formula (IVd).

The operating procedure is the same as for the synthesis of amino phosphonate (IVa). The yield is 46% based on the enone. The characteristics of the product obtained are as follows:

NMR $^1$H (60 MHz)(CDCl$_3$): δ (ppm):

1.10 and 1.20 (d, J(H P)=16 Hz, 3H, methyl in C$_1$ (diastereoisomers), 1.30 (, 6H, methyls of phosphonate), 1.68 (s, 5H, methyl in C$_4$ and protons of the amine (displaced by D$_2$O)), 2.0 to 2.4 (massive, 2H protons in C$_2$), 3.2 to 3.8 (massive, 1H, benzyl proton), 4.05 (m, 4H, protons of the methylenes of phosphonate), 7.05 (massive, 5H, protons of phenyl).

NMR $^{31}$P(CDCl$_3$): δ (ppm) 30.12 and 30.21.

TOBER is then obtained as described in example 1. The diastereoisomers are separated by silica column chromatography, Merck 60-H, with the ethyl ether eluant 80 parts and petroleum ether 20 parts.

EXAMPLE 3

As described in example 1, the TANAPE radical was produced starting from the amine (IIIb). TANAPE is a pale orange oil with the following characteristics:

EPR (deoxygenated benzene): six lines
A($^{14}$N)=14.5 G, A($^{31}$P)=37.0 G, ΔH$_{pp}$=1.7 G
UV=241 nm (in acetonitrile)
Mass spectrum m/e (70 eV), 278 (M+), 263 (M+-CH$_3$), 141 (M+-P(O) (OEt)$_2$).

In the case of deuterated nitroxide radicals, the enones and dialkyl phosphonates for the production of deuterated amino alkenyl phosphonates, the precursors of the synthesis of the nitroxide radicals, must be deuterated. For example, hereinafter is given the synthesis diagram of the TOBER d$_{11}$ radical.

(a) Preparation of the deuterated benzalacetone of formula (VIIIc), given in appendix II Reaction takes place between the aldehyde of formula

in which Ph represents the phenyl radical and the deuterated acetone

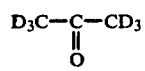

in the presence of deuterated soda (NaOD) in an aqueous solution in heavy water (D$_2$O). The compound (VIIIc) is obtained with a yield of 48% based on the deuterated acetone.

(b) Preparation of the alkenyl chloride of formula (VIIc), as shown in appendix II For this purpose, deuterated acetone is reacted with phosphorus pentachloride. Compound (VIIc) is obtained with a yield of 30% based on the deuterated acetone.

The deuterated benzalacetone (VIIIc) is then reacted with alkenyl chloride of formula (VIIc) in the presence of magnesium/cuprous iodide dissolved in tetrahydrofuran. This gives the deuterated enone of formula (VIc), given in the appendix, with a 35% percentage based on the benzalacetone of formula (VIIIc).

(c) Preparation of deuterated dialkylphosphonate of formula

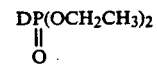

for reacting with the enone to form amino alkenylphosphonate (IVc), the precursor of the nitroxide radical.

For this purpose, triethyl phosphite (P(OCH$_2$CH$_3$)$_3$) is reacted with heavy water (D$_2$O) in acetonitrile. The yield of this reaction is 74% based on the triethyl phosphite.

A dialkyl phosphonate

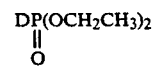

excess is then reacted with the enone of formula (VIc) in the presence of deuterated ammonia (ND$_3$), leading to the amino alkenylphosphonate of formula (IVc) given in appendix III with a 60% yield compared with the enone. As hereinbefore, the aminophosphorylation is carried out in HMPT heated to 50° in the presence of ammonium chloride and ND$_3$.

The amino alkenylphosphonate of formula (IVc) then undergoes a cyclizing aminomercuration reaction with mercuric acetate and then a demercuration by sodium hydridoborate, in the same way as described hereinbefore, with a 40% yield based on the amino alkenylphosphonate. The cyclic amine (IIIc) obtained is given in appendix III. It is then oxidized by m-chloroperbenzoic acid to finally give the TOBER d$_{11}$ radical with a 30% yield based on the starting amino alkenylphosphonate.

In an exemplified manner is given hereinafter the synthesis diagram of nitroxide radicals according to the invention of type (I), for which Y$_1$ represents —N= and Y$_2$ represents R$_4$—C=, called imidazoline-oxyl radicals, of formula (XII) given in appendix IV.

In particular a description is given of the reaction diagram leading to 2-diethoxyphosphoryl-2,3,5,5-tetramethyl-imidazoline-oxyl-1 (XIIa):

(a) Preparation of nitrophosphonate of formula (XIII) by acetylation of 2-diethoxyphosphoryl-2-nitroethane

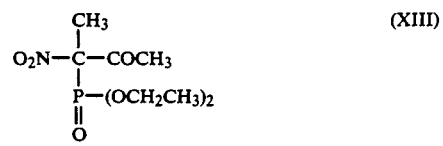

Reaction takes place between the acetyl chloride of formula CH$_3$—COCL with

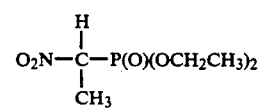

(b) A reduction of the compound (XIII) by zinc in the presence of NH₄Cl leading to the corresponding hydroxyl amine (XIV)

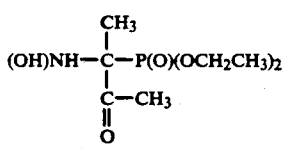

(c) Compound (XIV) is then treated according to the procedure described by L. B. VOLODARSKII in the book Biological Magnetic Resonance, L. J. BERLINER, J. REUBEN Ed., vol. 2, chapter 4, Plenum N.Y. A mixture of acetone and ammonia is added and then the cyclic hydroxyl amine obtained is oxidized.

For example, reference is made hereinafter to the method for obtaining nitroxide radicals according to the invention of type (I), for which $Y_1$ and $Y_2$ respectively represent $$R_6-C= \text{ and } R_4-C=.$$

This method is a so-called Favorsky cycle regression described in the article by M. DAGEONNEAU, Synthesis, pp. 895 to 916, 1984.

On the basis of a cyclic amine of formula (IIIe)

(IIIe)

obtained according to the process described hereinbefore, e.g. for the preparation of the TANAPE radical, the regression of the cycle takes place by iodine in the presence of potash. This reaction leads to an amine (IIIf) of formula (IIIf)

This amine is then oxidized according to the aforementioned process for obtaining TOMER.

For example, hereinafter is given the synthesis diagram of nitroxide radicals according to the invention of type (I) for which $Y_1$ represents an oxygen atom, whereas $Y_2$ exclusively represents

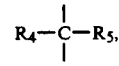

or of type (II) for which $Y_2$ represents an oxygen atom. These radicals are respectively represented by formulas (XV) and (XVI) in appendix IV.

In particular, a description is given of the reaction diagram leading to 4-diethoxyphosphoryl-2,2,4-trimethyl-oxazolidin-3-oxyl of formula (XVa) in appendix IV.

(a) Aminophosphorylation by a mixture of ammonia and diethyl phosphonate of the compound

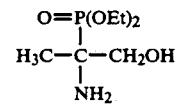

leads to the corresponding amino alcohol:

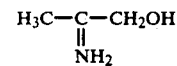

(b) A condensation of acetone, followed by a cyclization on the aforementioned amino alcohol leads to the cyclic amine (IIIg)

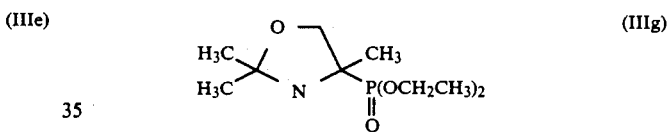

(c) The oxidation of amine (IIIg) leads to the nitroxide radical of formula (XVa).

TABLE

| Nitroxide radical | $\nu e$(MHz) | n | $\nu e/n$ Ratio to TANO d¹⁵N | EPR line width ($\mu$T) | SN radical/SN TANO d¹⁵N |
|---|---|---|---|---|---|
| TANO ¹⁴N | 61 | 6 | 0.7 | 55 | 0.75 |
| TANO d¹⁵N | 57 | 4 | 1 | 35 | 1 |
| TOMER | 166 | 12 | 0.97 | 150 | 0.55 |
| TOBER | 174 | 12 | 1.02 | 150 | 0.65 |
| TOBER d₁₁ | 174 | 12 | 1.02 | 65 | 1.2 |

APPENDIX I

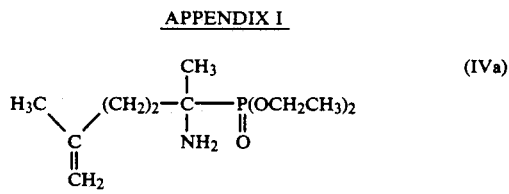

(IVa)

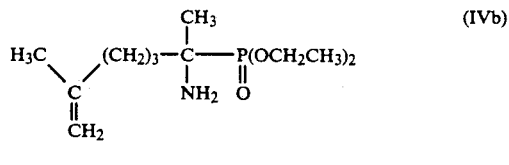

(IVb)

APPENDIX I (continued)
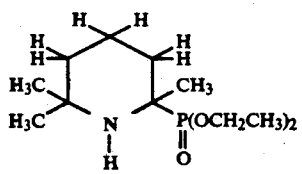 (IIIb)
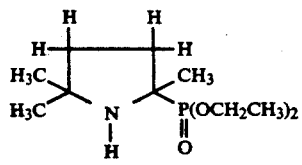 (IIIa)
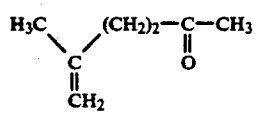 (VIa)
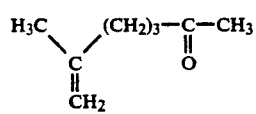 (VIb)
APPENDIX II
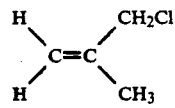 (VIIa)
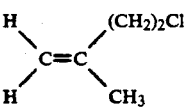 (VIIb)
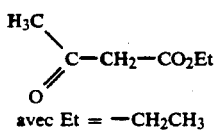 (VIIIa)
avec Et = —CH$_2$CH$_3$
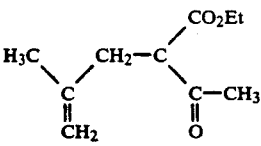 (IXa)
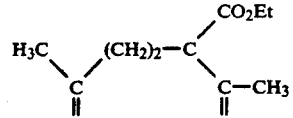 (IXb)
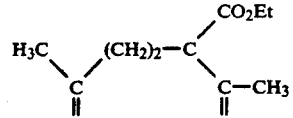 (VIIIc)
 (VIIc)
APPENDIX II (continued)
 (VIId)
 (VIIId)
APPENDIX III
 (VIc)
 (IVc)
Ph = phenyl radical
 (IIIc)
 (IVd)
 (IIId)
 (VId)
APPENDIX IV
 (XII)

-continued
APPENDIX IV

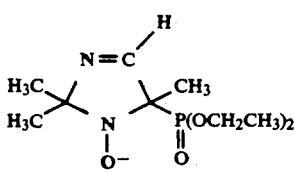 (XIIa)

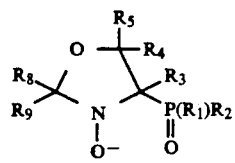 (XV)

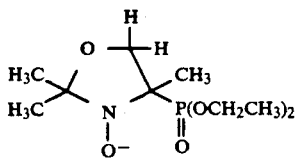 (XVa)

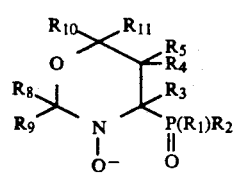 (XVI)

We claim:

1. A cyclic nitroxide radical having the formula (I):

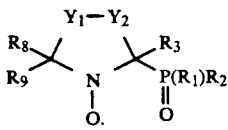 (I)

in which $Y_1$ represents

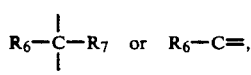

$Y_2$ represents

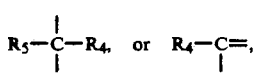

wherein when $Y_1$ represents

then $Y_2$ is

and when $Y_1$ represents

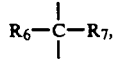

$Y_2$ is

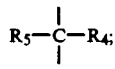

in which $R_1$ and $R_2$ are independently chosen from the group consisting of deuterated or undeuterated alkyl, alkoxyl, dialkylamino and phenyl groups, hydrogen atoms, deuterium or chlorine; $R_3$, $R_8$ and $R_9$ are independently selected from the group consisting of deuterated or undeuterated alkyl, alkoxyl and phenyl groups; $R_4$, $R_5$, $R_6$ and $R_7$ are each independently selected from the group consisting of deuterated or undeuterated alkyl, alkoxyl, dialkylamino and phenyl groups, COOH, OH, OD, H, D, a halogen, and COOR in which R is an alkyl group.

2. Nitroxide radical according to claim 1, wherein $R_1$ and $R_2$ independently represent an alkoxyl group with 1 to 6 carbon atoms; $R_3$, $R_8$ and $R_9$ independently represent a deuterated or undeuterated alkyl or phenyl group having 1 to 6 carbon atoms; and $R_4$, $R_5$, $R_6$, and $R_7$ independently represent H or D.

3. A nitroxide radical according to claim 1, wherein $R_1$ and $R_2$ are each —$OCH_2CH_3$; $R_3$, $R_8$ and $R_9$ are each $CH_3$; $Y_2$ is

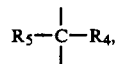

$R_4$, $R_5$ and $R_6$ are each H and $R_7$ is H or a phenyl group.

4. Nitroxide radical according to claim 1, wherein $R_1=R_2=OCH_2CH_3$; $R_3=R_8=R_9=CD_3$;

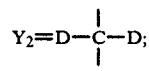

and

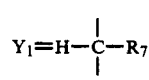

in which $R_7$ is a phenyl group.

* * * * *